United States Patent [19]
Collins et al.

[11] Patent Number: 6,048,853
[45] Date of Patent: *Apr. 11, 2000

[54] 1-ARYLPHTHALAZINE ANTAGONISTS OF EXCITATORY AMINO ACID RECEPTORS

[75] Inventors: Mark A. Collins, Frazer; Jeffrey C. Pelletier, Lafayette Hill, both of Pa.

[73] Assignee: Bearsden Bio, Inc., Aston, Pa.

[*] Notice: This patent is subject to a terminal disclaimer.

[21] Appl. No.: 08/588,549

[22] Filed: Jan. 18, 1996

[51] Int. Cl.[7] .................. C07D 237/30; C07D 491/056; A61K 31/50

[52] U.S. Cl. .................. 514/212; 514/248; 544/237; 544/234

[58] Field of Search .................. 544/237, 234; 514/212, 248

[56] References Cited

U.S. PATENT DOCUMENTS 5,716,956  2/1998  Pelletier .................. 544/237

OTHER PUBLICATIONS

Pelletier, J. Med Chem 39, 344 (1996).
Canon. Chem Abs. 101, 31117 b (1983).

(List continued on next page.)

*Primary Examiner*—Mark L. Berch
*Attorney, Agent, or Firm*—Arnall Golden & Gregory, LLP

[57] ABSTRACT

Substituted 1-arylphthalazine compositions with the formula

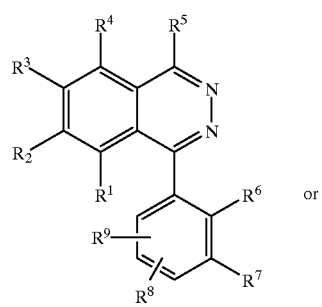

I

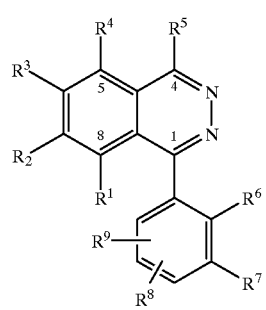

II wherein $R^1$, $R^2$, $R^3$ and $R^4$ are independently
  a) H,
  b) HO,
  c) $R^{11}O-$,
  d) halogen,
  e) C1–C3-alkyl,
  f) $CF_3$,
  g) $R^{12}CO_2-$, or
  h) $R^{12}CONH-$;

$R^1$ and $R^2$, or $R^2$ and $R^3$, or $R^3$ and $R^4$ can be taken together to be
  a) $-OCH_2O-$, or
  b) $-OCH_2CH_2O-$;

$R^5$ is
  a) H,
  b) C1–C6-alkyl,
  c) C3–C6-alkenyl,
  d) C3–C6-alkynyl,
  e) C3–C6-cycloalkyl,
  f) phenyl or substituted phenyl, wherein the phenyl is substituted with one or two substituents selected from the group consisting of C1–C3-alky, halogen, $R^{12}HN-$, $R^{12}O-$, $CF_3-$, $R^{13}SO_2-$ and $CO_2R^{12}$, or
  g) phenyl-C1–C3-alkyl or substituted phenyl-C1–C3-alkyl, wherein the phenyl is substituted with one or two substituents selected from the group consisting of C1–C3-alkyl, halogen, $R^{12}HN-$, $R^{12}O-$, $CF_3-$, $R^{13}SO_2-$ and $-CO_2R^{12}$;

$R^6$ is
  a) $R^{10}R^{11}N-$,
  b) $R^{10}NHC(NH)-$,
  c) $R^{12}CONH-$,
  d) 1-pyrrolidino or
  e) 1-piperidino;

$R^7$ is H;

$R^8$ and $R^9$ are independently
  a) H,
  b) C1–C3-alkyl,
  c) halogen,
  d) $R^{12}O-$,
  e) $CF_3-$, or
  f) $-CO_2R^{12}$;

$R^{10}$ and $R^{11}$ are independently
  a) H,
  b) C1–C10-alkyl,
  c) C1–C6-perfluoroalkyl,
  d) C3–C10-alkenyl,
  e) C3–C10-alkynyl, or
  f) C3–C6-cycloalkyl;

$R^{12}$ is H or C1–C3-alkyl; and
$R^{13}$ is C1–C3-alkyl or $CF_3$;

and pharmaceutically acceptable salts thereof,

11 Claims, No Drawings

OTHER PUBLICATIONS

McBurney, "Therapeutic Potential of NMDA Antagonists in Neurodegenerative Diseases," *Neurobiology of Aging*, 15:271–273 (1994).

Meldrum and Smith, "Cerebroprotective Effect of a Non–N–Methyl–D–Aspartate Antagonist, GYKI 52466, After Focal Ischemia in the Rat," *Stroke* 23:861 (1992).

Meldrum, "Excitatory Amino Acids in Epilepsy and Potential Novel Therapies," *Epilepsy Research*, 12:189–196 (1992).

Peillet et al., "The non–NMDA antagonists, NBOX and GYKI 52466, protect against cortical and striatal cell loss following transient global ischaemia in the rat," *Brain Res.*, 571:115 (1992).

Rogawski et al., "Anticonvulsant Activity of AMPA/kainate antagonists:Comparison of GYKI 52466 and NBOX In Maximal Electroshock and Chemoconvulsant Seizure Models," *Epilepsy Research*, 15:179–184 (1993).

Tarnawa et al., "Electrophysiological Studies With a 2,3–benzodiazepine Muscle Relaxant:GYKI 52466," *Eur. J. Pharmacol.*, 167:193–199 (1989).

Donevan and Rogawski, "GYKI 52466, a 2,3–Bensodiazepine, Is a Highly Selective, Noncompetitive Antagonist of AMPA/kainate Receptor Responses," *Neuron*, 10:51–59 (1993).

Hussy and et al., "Functional Properties Of A Cloned 5–hydroxytryptamine Ionotropic Receptor Subunit:Comparison With Native Mouse Receptors," *J. Physiol.* (Lond.), 481.2:311–323 (1994).

Lipton and Rosenberg, "Excitatory Amino Acids As A Final Common Pathway For Neurologic Disorders," *New England Journal of Medicine*, 330:613–622 (1994).

Chen et al., "Evaluation of Five Methods for Testing Anticonvulsant Activities," *Proc, Soc. Exp. Biol. Med.*, 87:334 (1954).

1-ARYLPHTHALAZINE ANTAGONISTS OF EXCITATORY AMINO ACID RECEPTORS

BACKGROUND OF THE INVENTION

The present invention relates generally to phthalazirie compounds useful as AMPA receptor antagonists, which are useful for the treatment of neuropsychopharmacological disorders such as stroke, ischemia, epilepsy and mood disorders.

In the past fifteen years a great deal of attention has been directed toward the excitatory amino acids (EAA's), glutamate and aspartate, since they are believed to be the neurotransmitter responsible for fast excitatory transmission in the mammalian central nervous system (CNS). At present the ionotropic EAA receptors are generally sub-classified into NMDA and non-NMDA receptors. This classification defines those receptors which preferentially bind N-methyl-D-aspartate (NMDA) and those that are not responsive to NMDA but responsive to α-amino-3-hydroxy-5-methyl-4-isoxazoleproprionic acid (AMPA) and kainic acid (KA).

Tarnawa et al. describe 2,3-benzodiazepines (*Eur. J. Pharmacol.*, 167:193–199, 1989) which inhibit AMPA stimulated cunents in neuronal cells. The 2,3-benzodiazepines such as GYKI 52466 and 53655 described by Tarnawa are non-competitive AMPA antagonists which bind to a novel modulatory site on the AMPA receptor. Meldrum (*Stroke*, 23:861, 1992 & *Brain Res.*, 571:115, 1992) has shown that GYKI 52466 was effective in rat models of both global and focal ischemia. GYKI 52466 was effective in a middle cerebral artery occlusion (MCAO) model of ischiemia when given either continuously for 2 hours just after occlusion or ore hour after occlusion. They reduced cortical infarct volumes by 68% and 48% respectively. In another model of neurodegenerative disease, the rat common carotid arteries model of global ischemia, GYKI 52466 was as effective as the glutamate site competitive antagonist NBQX. These animal models suggest that these compounds may be useful for the treatment of stroke and neurodegenerative conditions following ischemia. Parsons and Truner (GB 1,094,044) describe 1-(N-hydroxyamino)-phthalazines which have antipyretic, antiinflammatory, and hypotensive properties.

Efforts to find NMDA receptor antagonists and blockers which are neuroprotective have been very successful while efforts to find specific non-NMDA receptor antagonists have been much less successful. A number of pharmaceutical companies have pursued development of ion channel blockers or full antagonists of the NMDA receptor to protect against both chronic and acute neurodegenerative processes. Although some compounds entered clinical trials there has been only limited progress in developing a clinically useful NMDA receptor antagonist, because the compounds exhibit severe side effects ranging from hallucinations and loss of coordination, to neuronal damage, memory impairment and learning disability. Though non-NMDA antagonists have been shown to be useful in neuroprotective models in animals, there has been little progress in developing a clinically useful AMPA receptor antagonist.

It is an object of the invention to provide compounds which are useful as non-NMDA receptor antagonists as well as methods for their synthesis. It is a further object of the invention to provide non-NMDA receptor antagonists which are useful as sedatives or for the treatment of neuropsychopharmacological disorders such as stroke, ischemia, epilepsy and mood disorders. It is yet another object of the invention to provide compounds which are useful for the treatment of neurological, neuropsychiatric, neurogenerative, and functional disorders associated with excessive activation of the non-NMDA subtypes of the ionotropic EAA receptor, particularly the AMPA subtype.

SUMMARY OF THE INVENTION

Compositions are provided which are active as non-NMDA ionotropic excitatory amino acid (EAA) receptor antagonists, in particular, which bind to the AMPA receptors, and which therefore are useful for treating disorders associated with excessive activation of the non-NMDA subtypes of the ionotropic EAA receptors. The compounds further are useful as testing agents to identify and characterize other compounds for the treatment of these disorders.

Illustrative compounds include:

1-(3-aminophenyl)-6,7-methylenedioxyphthalazine,
1-(3-amino-4-methylphenyl)-6,7-methylenedioxyphthalazine,
1-(3-amino-4-chlorophenyl)-6,7-methylenedioxyphthalazine,
1-(3-aminophenyl)-6-methoxyphthalazine,
1-(3-amino-4-methylphenyl)-6-methoxyphthalazine,
1-(3-amino-4-chlorophenyl)-6-methoxy-phthalazine,
1-methyl-4-(3-aminophenyl)-6,7-methylenedioxyphthalazine,
1-methyl-4-(3-amino-4-methylphenyl)-6,7-methylenedioxyphthalazine,
1-methyl-4-(3-amino-4-chlorophenyl)-6,7-methyleneliioxyphthalazine,
1-ethyl-4-(3-aminophenyl)-6,7-methylenedioxyphthlaazine,
1-methyl-4-(3-aminophenyl)-6-methoxyphthalazine,
1-methyl-4-(3-amino-4-methylphenyl)-6-methoxyphthalazine,
1-methyl-4-(3-amino-4-chlorophenyl)-6-methoxyphthalazine, and
1-ethyl-4-(3-aminophenyl)-6-methoxyphthalazine.

The compounds may be provided in combination with a suitable pharmaceutical carrier for oral or parenteral administration. The compounds may be administered orally or parenterally for the treatment of a variety of disorders associated with non-NMDA EAA receptor function. The compositions may be used, for example, as sedatives or for the treatment of neuropsychopharmacological disorders such as stroke, ischemia, epilepsy and mood disorders.

DETAILED DESCRIPTION OF THE INVENTION

I. Glossary of Terms

The following terms are defined so that their use in this application is unambiguous:

The term "antagonist" as used herein means any compound which reduces the flow of cations through the non-NMDA receptors.

The term "neuropsychopharmacological disorder" as used herein means a disorder resulting from or associated with an excessive flux of ions through the AMPA receptor ligand-gated cation channel, and includes chemical toxicity (including substance tolerance and addiction), excitotoxicity, neurodegenerative disorders (such as Huntington's disease, Parkinson's disease, and Alzheimer's disease), post-stroke sequelae, epilepsy, seizures, mood disorders (such as bipolar disorder, dysthymia, and seasonal affective disorder), and depression. Neurodegenerative disorders can result from dysfunction or malfunction of non-NMDA receptor.

The term "NMDA receptor" as used herein means a receptor which is stimulated, at a minimum, by the excitatory amino acids glutamic acid as well as by NMDA, but is not stimulated by AMPA or ktinic acid. It is a ligand-gated receptor.

The term "AMPA receptor" as used herein means a receptor which is stimulated, at a minimum, by the excitatory amino acids glutamic acid as well as by AMPA, but is not stimulated by NMDA. It is a ligand-gated receptor.

The term "Kainate receptor" as used herein means a receptor which is stimulated, at a minimum, by the excitatory amino acids glutamic acid as well as by kainic acid, but is not stimulated by NMDA. It is a ligand-gated receptor.

Pharmaceutically acceptable salts include both the metallic (inorganic) salts and organic salts; a list of which is given in Remingyton's Pharmaceutical Sciences 17th Edition, p. 1418 (1985). It is well known to one skilled in the art that an appropriate salt form is chosen based on physical and chemical stability, flowability, hydroscopicity and solubility.

Throughout this application when an alkyl substituent is identified, the normal alkyl structure is intended (i.e., butyl is n-butyl) unless otherwise specified. However, when radicals are identified (e.g., $R^5$), both branched and straight chains are included in the definition of alkyl, alkenyl, and alkynyl.

II. Compositions with Non-NMDA EAA Receptor Antagonist Properties

A. Compounds of Formula I

Compounds of Formula I are provided which can be active as non-NMDA EAA receptor antagonists.

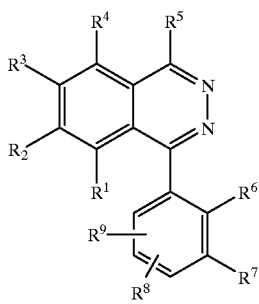

I wherein $R^1$, $R^2$, $R^3$ and $R^4$ are independently
 a) H,
 b) HO,
 c) $R^{11}O$—,
 d) halogen (F, Cl, Br),
 e) C1–C3-alkyl,
 f) $CF_3$,
 g) $R^{12}CO_2$—, or
 h) $R^{12}CONH$—;

$R^1$ and $R^2$, or $R^2$ and $R^3$, or $R^3$ and $R^4$ can be taken together to be
 a) —$OCH_2O$—, or
 b) —$OCH_2CH_2O$—;

$R^5$ is
 a) H,
 b) C1–C6-alkyl,
 c) C3–C6-alkenyl,
 d) C3–C6-alkynyl,
 e) C3–C6-cycloalkyl,
 f) phenyl or substituted phenyl, where the phenyl is substituted with one or two substituents, C1–C3-alkyl, halogen (F, Cl, Br), $R^{12}HN$—, $R^{12}O$—, $CF_3$—, $R^{13}SO_2$— or $CO_2R^{12}$, or
 g) phenyl-C1–C3-alkyl or substituted phenyl-C1–C3-alkyl, where the phenyl is substituted with one or two substituents, C1–C3-alkyl, halogen (F, Cl, Br), $R^{12}HN$—, $R^{12}O$—, $CF_3$—, $R^{13}SO_2$— or, —$CO_2R^{12}$;

$R^6$ is
 a) $R^{10}R^{11}N$—,
 b) $R^{10}NHC(NH)$—, or
 c) $R^{12}CONH$—;

$R^7$ is H;

$R^8$ and $R^9$ are independently
 a) H,
 b) C1–C3-alkyl,
 c) halogen (F, Cl, Br),
 d) $R^{12}O$—,
 e) $CF_3$—, or
 f) —$CO_2R^{12}$;

$R^{10}$ and $R^{11}$ are independently
 a) H,
 b) C1–C10-alkyl,
 c) C1–C6-perfluoroalkyl,
 d) C3–C10-alkenyl,
 e) C3–C10-alkynyl, or
 f) C3–C6-cycloalkyl;

$R^{10}$ and $R^{11}$ taken together are a ring of 5–6-carbons;

$R^{12}$ is H or C1–C3-alkyl; and $R^{13}$ is C1–C3-alkyl or $CF_3$;

and pharmaceutically acceptable salts thereof.

Preferred compounds are compounds of Formula I wherein:

$R^1$, $R^2$, $R^3$ and $R^4$ are independently H, $R^{11}O$—, halogen (F, Cl, Br), or C1–C3-alkyl;

$R^2$ and $R^3$ taken together can be —$OCH_2O$—;

$R^6$ is $R^{10}R^{11}N$; and $R^8$ and $R^9$ are H, and pharmaceutically acceptable salts thereof.

Specifically preferred compounds are:

1-(2-aminophenyl)-6,7-methylenedioxyphthalazine, 1-(2-amino-4-methylphenyl)-6,7-methylenedioxyphthalazine, 1-(2-amino-4-chlorophenyl)-6,7-methylenedioxyphthalazine, 1-(2-aminophenyl)-6-methoxyphthalazine, 1-(2-amino-4-methylphenyl)-6-methoxyphthalazine, 1-(2-amino-4-chlorophenyl)-6-methoxy-phthalazine, 1-methyl-4-(2-aminophenyl)-6,7-methylenedioxyphthalazine, 1-methyl-4-(2-amino-4-methylphenyl)-6,7-methylenedioxyphthalazine, 1-methyl-4-(2-amino-4-chlorophenyl)-6,7-methylenedioxyphthalazine, 1-ethyl-4-(2-aminophenyl)-6,7-methylenedioxyphthalazine, 1-methyl-4-(2-aminophenyl)-6-methoxyphthalazince, 1-methyl-4-(2-amino-4-methylphenyl)-6-methoxyphthalazine, 1-methyl-4-(2-amino-4-chlorophenyl)-6-methoxyplithalazine, and 1-ethyl-4-(2-aminophenyl)-6-methoxyphthalazine.

The compounds of Formula I may be combined with a suitable pharmaceutical carrier and used to treat neurological, neuropsychological, neuropsychiatric, neurodegenerative, neuropsychopharmacological and functional disorders associated with excessive activation of the non-NMDA subtype of the ionotropic EAA receptors. The compounds also may be used as testing agents to identify and characterize other compounds for the treatment of acute and chronic neurodegenerative diseases, seizures, depression, anxiety and substance addiction.

B. Compounds of Formula II

In another embodiment, compounds of Formula II are provided, in combination with a suitable pharmaceutical carrier, which may be used in methods for the treatment of neurological, neuropsychological, neuropsychiatric, neurodegenerative, neuropsychopharmacological and functional disorders associated with excessive activation of the non-NMDA subtype of the ionotropic EAA receptors. The compounds also may be used as testing agents to identify and characterize other compounds for the treatment of acute and chronic neurodegenerative disease, seizures, depression, anxiety and substance addiction.

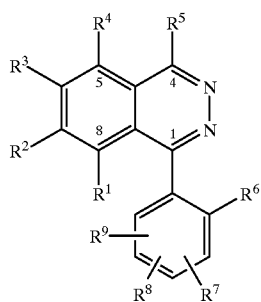

II wherein $R^1$, $R^2$, $R^3$ and $R^4$ are independently
  a) H,
  b) HO,
  c) $R^{11}O$—,
  d) halogen (F, Cl, Br),
  e) C1–C3-alkyl,
  f) $CF_3$,
  g) $R^{12}CO_2$—, or
  h) $R^{12}CONH$—;

$R^1$ and $R^2$, or $R^2$ and $R^3$, or $R^3$ and $R^4$ can be taken together to be
  a) —$OCH_2O$—, or
  b) —$OCH_2CH_2O$—;

$R^5$ is
  a) H,
  b) C1–C6-alkyl,
  c) C3–C6-alkenyl,
  d) C3–C6-alkynyl,
  e) C3–C6-cycloalkyl,
  f) phenyl or substituted phenyl, where the phenyl is substituted with one or two substituents, C1–C3-alkyl, halogen (F, Cl, Br), $R^{12}HN$—, $R^{12}O$—, $CF_3$—, $R^{13}SO_2$— or $CO_2R^{12}$, or
  g) phenyl-C1–C3-alkyl or substituted phenyl-C1–C3-alkyl, where the phenyl is substituted with one or two substituents, C1–C3-alkyl, halogen (F, Cl, Br), $R^{12}HN$—, $R^{12}O$—, $CF_3$—, $R^{13}SO_2$— or, —$CO_2R^{12}$;

$R^6$ and $R^7$ are independently
  a) H
  b) $R^{10}R^{11}N$—,
  c) $R^{10}NHC(NH)$—, or
  d) $R^{12}CONH$—;

$R^8$ and $R^9$ are independently
  a) H,
  b) C1–C3-alkyl,
  c) halogen (F, Cl, Br),
  d) $R^{12}O$—,
  e) $CF_3$—, or
  f) —$CO_2R^{12}$;

$R^{10}$ and $R^{11}$ are independently
  a) H,
  b) C1–C10-alkyl,
  c) C1–C6-perfluoroalkyl,
  d) C3–C10-alkenyl,
  e) C3–C10-alkynyl, or
  f) C3–C6-cycloalkyl;

$R^{10}$ and $R^{11}$ taken together are a ring of 5–6-carbons;

$R^{12}$ is H or C1–C3-alkyl; and $R^{13}$ is C1–C3-alkyl or $CF_3$;

and pharmaceutically acceptable salts thereof, with the proviso that $R^6$ and $R^7$ cannot both be H.

Specifically preferred compounds include:

1-(3-aminophenyl)-6,7-methylenedioxyphthalazine,
1-(3-amino-4-methylphenyl)-6,7-methylenedioxyphthalazine,
1-(3-amino-4-chlorophenyl)-6,7-methylenedioxyplithalazine,
1-(3-aminophenyl)-6-methoxyphthalazine,
1-(3-amino-4-methylphenyl)-6-methoxyphthalazine,
1-(3-amino-4-chlorophenyl)-6-methoxyphthalazine,
1-methyl-4-(3-aminophenyl)-6,7-methylenedioxyphthalazine,
1-methyl-4-(3-amino-4-methylphenyl)-6,7-methylenedioxyphthalazine,
1-methyl-4-(3-amino-4-chlorophenyl)-6,7-methylenedioxyphthalazine,
1-ethyl-4-(3-aminophenyl)-6,7-methylenedioxyphthalazine,
1-methyl-4-(3-aminophenyl)-6-methoxyphthalazine,
1-methyl-4-(3-amino-4-methylphenyl)-6-methoxyphthalazine,
1-methyl-4-(3-amino-4-chlorophenyl)-6-methoxyphthalazine,
1-ethyl-4-(3-aminophenyl)-6-methoxyphthalazine,
1-(4-aminophenyl)-6,7-methylenedioxyphthalazine,
1-(4-acetylaminophenyl)-6,7-methylenedioxyphthalazine,
4-(4-aminophenyl)-1-methyl-6,7-methylenedioxyphthalazine,
4-(4-acetylaminophenyl)-1-methyl-6,7-methylenedioxyphthalazine,
1-(4-aminophenyl)-7-methoxyphthalazine,
1-(4-acetylaminophenyl)-7-methoxyphthalazine,
4-(4-aminophenyl)-1-methyl-7-methoxyphthalazine, and
4-(4-acetylaminophenyl)-1-methyl-,7-methoxyphthalazine.

III. Synthesis

The compounds of Formula I or Formula II may be prepared using the reactions and techniques described in this section. The reactions are performed in solvent suitable to the reagents and materials employed and suitable for the transformation being effected. Depending upon the synthetic route selected, and the functionality of the starting material or intermediates, the appropriate protection groups and deprotection conditions available in the art of organic synthesis may be utilized in the synthesis of the compound.

In one embodiment, the compound of Formula II may be synthesized as outlined in Scheme 1. Protected aldehydes 3 can be prepared from commercially available aldehydes or aldehydes known in the literature by halogenating the aldehyde by treatment with bromine in a solvent such as acetic acid at a temperature from 0 to 35° C. for 6–24 hours. The aldehyde is then protected by a group such as an acetal by treatment of 2 with an alcohol such as ethylene glycol or ethanol in an inert solvent such as toluene with a catalytic amount of an acid such as p-toluensulfonic acid at the reflux temperature of the mixture with an apparatus to remove the water.

Protected amides 7 can be prepared from appropriate acids or acid chlorides by treatment of the acid chloride or acid anhydride with N, O-dimethylhydroxylamine in an inert solvent such as methylene chloride or tetrahydrofuran and a base such a pyridine at a temperature of −10 to 0° C. for 1–8 hours. Amides 6 can be converted to anilines by reducing the nitro group by treatment of 5 with hydrogen and a catalyst such a 10% Pd/C or 5% Pt/C in a solvent such as methanol at a pressure from atmospheric pressure to 60 psi for 30 minutes to 6 hours. The aniline 6 can be protected as the imine by treatment with a ketone such a benzophenone or an imine such as benzophenone imine in an inert solvent such as toluene with an acid catalyst such as boron trifluoride at a temperature from 20° C. to the reflux of the solvent for 2–8 hours.

The substituted benzophenones 8 are prepared by reacting the lithiated derivative of 3, which is generated by reacting 3 with a reagent such as n-butyl lithium in an inert solvent such as tetrahydrofuran at a temperature of −110 to −45° C. for 10–60 minutes, with amides 7 at a temperature of −78 to 25° C. for 2–24 hours. The benzophenones 8 are then converted to phthalazines 9 by treatment with hydrazine or hydrazine hydrochloride in a solvent such as methanol at a temperature of 0 to 35° C. for 6–24 hours.

SCHEME I

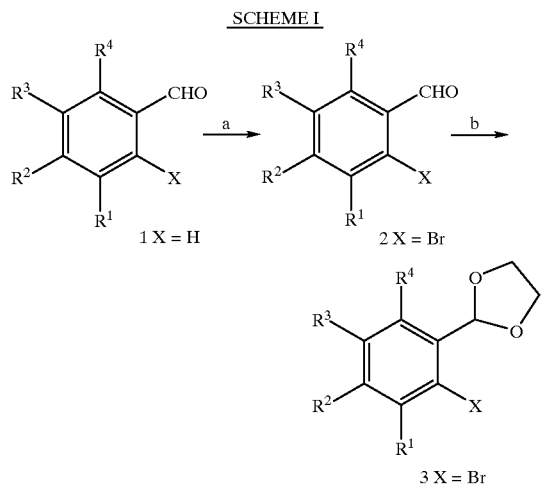

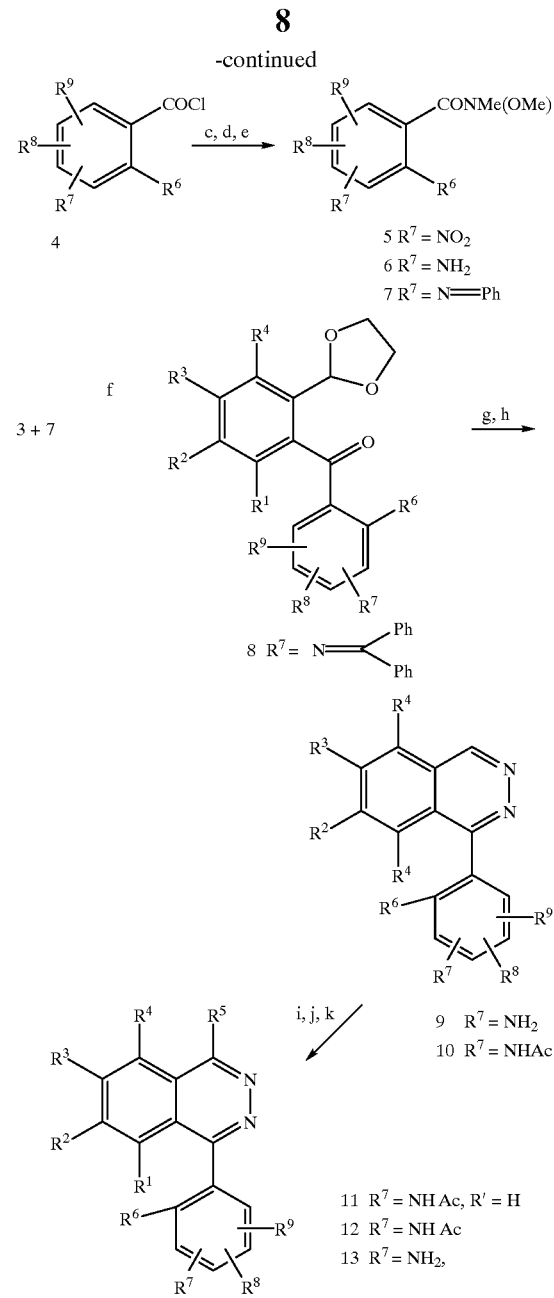

Reagents and Conditions: a) Br$_2$, AcOH; b) Eth. glycol, TsOH, tol., reflux; c) HNMe(OMe) HCl, pyr., DCM; d) H$_2$, Pd/C, MeOH; e) Benzophenoneimine, BF$_3$ OEt$_2$, tol., reflux; f) n-BuLi, THF, -78° C.; g) H$_2$NNH$_2$ HCl, MeOH—H$_2$O; h) Ac$_2$O; i) MeLi (Et$_2$O), TMEDA, THF, 0° C.; j) [O], PtO; k) 1N NaOH, MeOH.

The phthalazines can be further modified by first protecting the phthalazine anilines 9 with an amine protecting group such as acetyl by treatment with acetic anhydride either neat or in an inert solvent such as tetrahydrofuran at a temperature of 0° C. to reflux of the solvent for 2–12 hours. The protected phthalazine 10 is then treated with an alkyl lithium or Grignard reagent in an inert solvent such as tetrahydrofuran at a temperature of −78 to 25° C. for 1–6 hours. The dihydrophthalazines 11 can then be oxidized back to the phthalazines 12 by treatment with PtO in a solvent such as THF at a temperature of 25° C. to reflux of the solvent for 2–24 hours. The aniline protecting group is removed by treatment with a base such as NaOH in an aqueous solvent such as methanol at a temperature of 25° C. to reflux of the solvent for 2–14 hours.

Examples of compounds of Formula II are shown in Table 1, which were prepared or can be prepared by the methods outlined in Scheme 1 and described above and in the Examples below using the appropriate starting materials and reagents.

TABLE 1

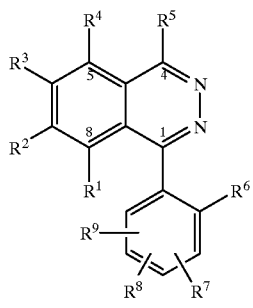

Phthalazines of Formula II

| EX. | $R^1, R^2, R^3, R^4$ | $R^5$ | $R^6$ | $R^7$ | $R^8, R^9$ | Anal. |
|---|---|---|---|---|---|---|
| 1 | 6,7-methylenedioxy | H | H | 3-$NH_2$ | H, H | NMR, IR |
| 2 | 6,7-methylenedioxy | Me | H | 3-$NH_2$ | H, H | |
| 3 | 6,7-methylenedioxy | Et | H | 3-$NH_2$ | H, H | |
| 4 | 6,7-methylenedioxy | Bu | H | 3-$NH_2$ | H, H | |
| 5 | 6,7-methylenedioxy | H | Me | 3-$NH_2$ | H, H | |
| 6 | 6,7-methylenedioxy | Me | Me | 3-$NH_2$ | H, H | |
| 7 | 6,7-methylenedioxy | Et | Me | 3-$NH_2$ | H, H | |
| 8 | 6,7-methylenedioxy | Bu | Me | 3-$NH_2$ | H, H | |
| 9 | 6,7-methylenedioxy | H | H | 3-$NH_2$ | 5-Cl, H | |
| 10 | 6,7-methylenedioxy | Me | H | 3-$NH_2$ | 5-Cl, H | |
| 11 | 6,7-methylenedioxy | Et | H | 3-$NH_2$ | 5-Cl, H | |
| 12 | 6,7-methylenedioxy | Bu | H | 3-$NH_2$ | 5-Cl, H | |
| 13 | 6,7-methylenedioxy | H | H | 3-$NH_2$ | 5-MeO, H | |
| 14 | 6,7-methylenedioxy | Me | H | 3-$NH_2$ | 5-MeO, H | |
| 15 | 6,7-methylenedioxy | Et | H | 3-$NH_2$ | 5-MeO, H | |
| 16 | 6,7-methylenedioxy | Bu | H | 3-$NH_2$ | 5-MeO, H | |
| 17 | 7-methoxy | H | H | 3-$NH_2$ | H, H | |
| 18 | 7-methoxy | Me | H | 3-$NH_2$ | H, H | |
| 19 | 7-methoxy | Et | H | 3-$NH_2$ | H, H | |
| 20 | 7-methoxy | Bu | H | 3-$NH_2$ | H, H | |
| 21 | 7-methoxy | H | Me | 3-$NH_2$ | H, H | |
| 22 | 7-methoxy | Me | Me | 3-$NH_2$ | H, H | |
| 23 | 7-methoxy | Et | Me | 3-$NH_2$ | H, H | |
| 24 | 7-methoxy | Bu | Me | 3-$NH_2$ | H, H | |
| 25 | 7-methoxy | H | H | 3-$NH_2$ | 5-Cl, H | |
| 26 | 7-methoxy | Me | H | 3-$NH_2$ | 5-Cl, H | |
| 27 | 7-methoxy | Et | H | 3-$NH_2$ | 5-Cl, H | |
| 28 | 7-methoxy | Bu | H | 3-$NH_2$ | 5-Cl, H | |
| 29 | 7-methoxy | H | H | 3-$NH_2$ | 5-MeO, H | |
| 30 | 7-methoxy | Me | H | 3-$NH_2$ | 5-MeO, H | |
| 31 | 7-methoxy | Et | H | 3-$NH_2$ | 5-MeO, H | |
| 32 | 7-methoxy | Bu | H | 3-$NH_2$ | 5-MeO, H | |
| 33 | 7-methyl | H | H | 3-$NH_2$ | H, H | |
| 34 | 7-methyl | Me | H | 3-$NH_2$ | H, H | |
| 35 | 7-methyl | Et | H | 3-$NH_2$ | H, H | |
| 36 | 7-methyl | Bu | H | 3-$NH_2$ | H, H | |
| 37 | 7-methyl | H | Me | 3-$NH_2$ | H, H | |

TABLE 1-continued

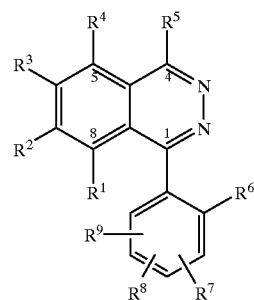

Phthalazines of Formula II

| EX. | $R^1, R^2, R^3, R^4$ | $R^5$ | $R^6$ | $R^7$ | $R^8, R^9$ | Anal. |
|---|---|---|---|---|---|---|
| 38 | 7-methyl | Me | Me | 3-$NH_2$ | H, H | |
| 39 | 7-methyl | Et | Me | 3-$NH_2$ | H, H | |
| 40 | 7-methyl | Bu | Me | 3-$NH_2$ | H, H | |
| 41 | 7-methyl | H | H | 3-$NH_2$ | 5-Cl, H | |
| 42 | 7-methyl | Me | H | 3-$NH_2$ | 5-Cl, H | |
| 43 | 7-methyl | Et | H | 3-$NH_2$ | 5-Cl, H | |
| 44 | 7-methyl | Bu | H | 3-$NH_2$ | 5-Cl, H | |
| 45 | 7-methyl | H | H | 3-$NH_2$ | 5-MeO, H | |
| 46 | 7-methyl | Me | H | 3-$NH_2$ | 5-MeO, H | |
| 47 | 7-methyl | Et | H | 3-$NH_2$ | 5-MeO, H | |
| 48 | 7-methyl | Bu | H | 3-$NH_2$ | 5-MeO, H | |
| 49 | 6,7-methylenedioxy | H | H | 4-$NH_2$ | H, H | NMR, IR |
| 50 | 6,7-methylenedioxy | Me | H | 4-$NH_2$ | H, H | NMR, IR |
| 51 | 6,7-methylenedioxy | Et | H | 4-$NH_2$ | H, H | |
| 52 | 6,7-methylenedioxy | Bu | H | 4-$NH_2$ | H, H | |
| 53 | 6,7-methylenedioxy | H | Me | 4-$NH_2$ | H, H | |
| 54 | 6,7-methylenedioxy | Me | Me | 4-$NH_2$ | H, H | |
| 55 | 6,7-methylenedioxy | Et | Me | 4-$NH_2$ | H, H | |
| 56 | 6,7-methylenedioxy | Bu | Me | 4-$NH_2$ | H, H | |
| 57 | 6,7-methylenedioxy | H | H | 4-$NH_2$ | 5-Cl, H | |
| 58 | 6,7-methylenedioxy | Me | H | 4-$NH_2$ | 5-Cl, H | |
| 59 | 6,7-methylenedioxy | Et | H | 4-$NH_2$ | 5-Cl, H | |
| 60 | 6,7-methylenedioxy | Bu | H | 4-$NH_2$ | 5-Cl, H | |
| 61 | 6,7-methylenedioxy | H | H | 4-$NH_2$ | 5-MeO, H | |
| 62 | 6,7-methylenedioxy | Me | H | 4-$NH_2$ | 5-MeO, H | |
| 63 | 6,7-methylenedioxy | Et | H | 4-$NH_2$ | 5-MeO, H | |
| 64 | 6,7-methylenedioxy | Bu | H | 4-$NH_2$ | 5-MeO, H | |
| 65 | 7-methoxy | H | H | 4-$NH_2$ | H, H | |
| 66 | 7-methoxy | Me | H | 4-$NH_2$ | H, H | |
| 67 | 7-methoxy | Et | H | 4-$NH_2$ | H, H | |
| 68 | 7-methoxy | Bu | H | 4-$NH_2$ | H, H | |
| 69 | 7-methoxy | H | Me | 4-$NH_2$ | H, H | |
| 70 | 7-methoxy | Me | Me | 4-$NH_2$ | H, H | |
| 71 | 7-methoxy | Et | Me | 4-$NH_2$ | H, H | |
| 72 | 7-methoxy | Bu | Me | 4-$NH_2$ | H, H | |
| 73 | 7-methoxy | H | H | 4-$NH_2$ | 5-Cl, H | |
| 74 | 7-methoxy | Me | H | 4-$NH_2$ | 5-Cl, H | |
| 75 | 7-methoxy | Et | H | 4-$NH_2$ | 5-Cl, H | |
| 76 | 7-methoxy | Bu | H | 4-$NH_2$ | 5-Cl, H | |
| 77 | 7-methoxy | H | H | 4-$NH_2$ | 5-MeO, H | |
| 78 | 7-methoxy | Me | H | 4-$NH_2$ | 5-MeO, H | |
| 79 | 7-methoxy | Et | H | 4-$NH_2$ | 5-MeO, H | |
| 80 | 7-methoxy | Bu | H | 4-$NH_2$ | 5-MeO, H | |

TABLE 1-continued

Phthalazines of Formula II

| EX. | $R^1, R^2, R^3, R^4$ | $R^5$ | $R^6$ | $R^7$ | $R^8, R^9$ | Anal. |
|---|---|---|---|---|---|---|
| 81 | 7-methyl | H | H | 4-NH$_2$ | H, H | |
| 82 | 7-methyl | Me | H | 4-NH$_2$ | H, H | |
| 83 | 7-methyl | Et | H | 4-NH$_2$ | H, H | |
| 84 | 7-methyl | Bu | H | 4-NH$_2$ | H, H | |
| 85 | 7-methyl | H | Me | 4-NH$_2$ | H, H | |
| 86 | 7-methyl | Me | Me | 4-NH$_2$ | H, H | |
| 87 | 7-methyl | Et | Me | 4-NH$_2$ | H, H | |
| 88 | 7-methyl | Bu | Me | 4-NH$_2$ | H, H | |
| 89 | 7-methyl | H | H | 4-NH$_2$ | 5-Cl, H | |
| 90 | 7-methyl | Me | H | 4-NH$_2$ | 5-Cl, H | |
| 91 | 7-methyl | Et | H | 4-NH$_2$ | 5-Cl, H | |
| 92 | 7-methyl | Bu | H | 4-NH$_2$ | 5-Cl, H | |
| 93 | 7-methyl | H | H | 4-NH$_2$ | 5-MeO, H | |
| 94 | 7-methyl | Me | H | 4-NH$_2$ | 5-MeO, H | |
| 95 | 7-methyl | Et | H | 4-NH$_2$ | 5-MeO, H | |
| 96 | 7-methyl | Bu | H | 4-NH$_2$ | 5-MeO, H | |
| 97 | 6,7-methylenedioxy | H | H | 4-NHMe | H, H | |
| 98 | 6,7-methylenedioxy | Me | H | 4-NHMe | H, H | |
| 99 | 6,7-methylenedioxy | Et | H | 4-NHMe | H, H | |
| 100 | 6,7-methylenedioxy | Bu | H | 4-NHMe | H, H | |
| 101 | 6,7-methylenedioxy | H | H | 4-CH$_3$CONH | H, H | NMR, IR |
| 102 | 6,7-methylenedioxy | Me | H | 4-CH$_3$CONH | H, H | NMR, IR |
| 103 | 6,7-methylenedioxy | Et | H | 4-CH$_3$CONH | H, H | |
| 104 | 6,7-methyiene-dioxy | Bu | H | 4-CH$_3$CONH | H, H | |
| 105 | 6,7-methylenedioxy | H | NH$_2$ | H | H, H | |
| 106 | 6,7-methylenedioxy | Me | NH$_2$ | H | H, H | |
| 107 | 6,7-methylenedioxy | Et | NH$_2$ | H | H, H | |
| 108 | 6,7-methylenedioxy | Bu | NH$_2$ | H | H, H | |

IV. In Vitro and In Vivo Assays of Activity and Therapeutic Efficacy

In vivo and in vitro assays may be conducted to determine the activity the compounds as antagonists of the non-NMDA receptors, e.g., the otropic EAA receptors which bind AMPA. In combination, in vitro and vivo assays are predictive of the activity of these compounds for treatment patients. This is supported, for example, by numerous studies in the rature illustrating that in vitro and in vivo studies of NMDA receptor modulation by a test compound provide a good indication of the compound's efficacy in treating disorders associated with excessive activation of the NMDA receptor. See, e.g.: Meldrum, *Epilepsy Research*, 12:189–196 (1992); Lipton and Rosenberg, *New England Journal of Medicine*, 330:613–622 (1994); and McBurney, *Neurobiology of Aging*, 15:271–273 (1994).

Electrophysiology

This test determines the potency for drug inhibition of the AMPA receptor. The potency of compounds is tested using the whole-cell patch clamp technique on primary cultures of rat neocortex. The general procedure for stimulating AMPA-receptor mediated currents with KA and for the measurement of current inhibition is based on that used by Donevan and Rogawski (Neuron, 10: 51–59, 1993) for 2,3-benzodiazepines.

Standard extracellular bath solutions and intracellular pipette solutions are used as described in detail by Hussy and coworkers (*J. Physiol.* (Lond.), 481.2: 311–323, 1994). The drug application system is designed to allow rapid switching between 7 different reservoirs containing, either control bath solution, kainic acid (50 µM) or kainic acid (50 µM) plus antagonist (10 µM). Each recording is begun with a control response to kainic acid alone.

Following the establishment of a 2–3 sec duration steady baseline, bathing solution is switched to one containing kainic acid plus antagonist for an additional 2–3 sec period. Alternatively, 5 different (loses of a single compound are tested for the determination of the antagonist IC$_{50}$. The compound synthesized as described below in Example 1 was found to have a 48% AMPA receptor binding inhibition at 10 µM using this assay. Compounds which have a % inhibition greater than or equal to 20 at a dose of 10 µM are generally useful antagonists of the non-NMDA EAA receptors as disclosed herein.

Neurodegenerative Transient Global Forebrain Ischemia

This test is to measure the extent of protection by a test compound in a model of brain ischemia can be assayed as described in Meldrum et al., *Brain Res.*, 571:115, 1992, and references cited therein. Male Wistar rats (250–300 g) are anesthetized using halothane-oxygen-nitrogen mixture and both vertebral arteries are permanently occluded by elecro-cauterisation within the alar foraminae of the first cervical vertebra. At the same time, both common carotid arteries are isolated and atraumatic clamps placed around each one. One femoral vein is cannulated to enable the subsequent iv administration of fluid. The following day cerebral ischemia is induced in the unanaesthetised animal, by tightening the clamps around the carotid arteries for 20 min. Carotid clamping results. Body temperature is maintained at 37° C. by use of a rectal probe and hot plate. Seven days after the ischemic insult rats are sacrificed and the brains processed for light microscopy. Neuroprotection is assessed by examination of the extent of damage in the cortex and hippocampus. Compounds may be selected which are active in this model.

Neurodegenerative Permanent Focal Ischemia

The extent of protection by a test compound in a model of brain ischemia can be assayed as described by Meldrum and Smith (*Stroke*, 23:861, 1992), and references cited therein. Male Fisher F344 rats (210–310 g) are anesthetized with halothane-oxygen-nitrogen mixture receive a small incision between the eye and ear, the mandibular muscles are retracted to expose the orbit and zygomatic arch. A small craniotomy is made to expose the base of the middle cerebral artery. Bipolar coagulation is used to permanently occlude the artery at the base. One day after the ischemic insult rats are sacrificed and the brains processed for light microscopic examination. Lesion volume is determined by using Cavalarei's principle. Compounds may be selected which are active in this model.

Maximum Electro Shock (MES) Seizure Test

This test is to determine the extent of protection by a test compound in a seizure model. This model is described by Rogawski et al. (Epilepsy Research, 15:179–184, 1993). Male NIH Swiss mice (25–30 g) were injected ip with the test drug. The mice were subjected to a 0.2 sec, 60 Hz, 50 mA electrical stimulus delivered with corneal electrodes wetted with 0.9% saline at 15–30 min post dosing. Animals failing to show tonic hind limb extension were scored as protected. Compounds may be selected which are active in this model.

The results of this assay using compounds prepared as described in Examples 49, 50 and 102 are shown below in Table 2.

TABLE 2

MES Test Results

| Example | Dose (mg/kg) | Time (hours) | Score (protected/no. tested) |
|---|---|---|---|
| 49 | 3 | 0.5 | 1/1 |
|  | 15 | 2 | 2/4 |
| 50 | 1 | 4 | 1/7 |
| 102 | 100 | 4 | 3/3 |

Subcutaneous Metrazol (scMET) Seizure Test

This test is to determine the extent of protection by a test compound in a seizure model. The method used is that of Chen et al. (*Proc. Soc. Exp. Biol. Med.*, 87:334, 1954). Mice are randomly assigned to vehicle or treatment groups of 3–10 animals per group and then dosed accordingly. Metrazol (pentylenetetrazol) 90 mg/kg is administered subcutaneously (sc) at different time points (0.25, 0.5, 1, 2, 4 hr) after the treatment or control groups. The mice individually housed in clear runs and observed for the presence or absence of clonic seizure activity (>5 s duration) for 30 min after metrazol dosing. A compound is considered active if no seizure is observed. Data is analyzed using aquantal measure (protection/number tested).

The results of this assay using compounds prepared as described in Examples 49 and 50 are shown below in Table 3.

TABLE 3 scMET Test Results

| Example | Dose (mg/kg) | Time (hr) | Score (protect./no. tested) |
|---|---|---|---|
| 49 | 3 | 0.5 | 1/5 |
| 50 | 3 | 0.5 | 1/5 |

Dosage Forms

The compounds can be administered in combinatiion with standard pharmaceutically suitable carriers available in the art, by the appropriate route for the particular treatment. The compound can for example, be administered parenterally, i.e. subcutaneously, intramuscularly, or intravenously or, alternatively, administered orally in a dose range, for example, of about 0.01–100 mg/kg body weight.

The active ingredient can be administered parenterally, in sterile liquid dosage forms. In general, water, a suitable oil, saline, aqueous dextrose, and related sugar solutions and glycols such as propylene glycol or polyethylene glycols are suitable carriers for parenteral solutions. Solutions for parenteral administration preferably contain a water soluble form of the active ingredient, suitable stabilizing agents, and, if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkoniun chloride, methyl- or propylparaben, and chlorobutanol.

The active ingredient can be administered orally in solid dosage forms, such as capsules, tablets and powders, or in liquid dosage forms, such as elixirs, syrups, and suspensions. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide fcor continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. Suitable pharmaceutical carriers are described in Remington's Pharmaceutical Sciences, a. Osol, a standard reference text in this field.

Optionally, the compounds either alone or in combination with a carrier may be administered by implantation or by application to a mucosal surface, for example, the nasalpharyngeal region and/or lungs using an aerosol or may be administered to a skin surface via a topical carrier such as a cream or lotion.

The compounds of this invention and their preparation can be understood further by the following non-limiting examples. In these examples, unless otherwise indicated, all temperatures are in degrees Celsius and parts and percentages are by weight.

EXAMPLE 1

Synthesis of 1-(3-Aminophenyl)-6,7-methylenedioxyphthalazine

Part A. 2-Bromo-4,5-methylenedioxybenzaldehyde

Piperonal (30 g, 0.2 mol) was dissolved in glacial acetic acid and treated with a solution of bromine (80 g, 0.5 mol) in glacial acetic acid (100 mL). The resulting brown solution was stirred 16 hours at room temperature and then water (300 mL) was added. The solid precipitate was collected by filtration under reduced pressure, washed with water and recrystallized from 10% aqueous methanol (450 mL) to give the product (23 g, 50%) as white needles, mp 123–125° C. $^1$H NMR (200 MHz, CDCl$_3$) δ 10.18 (1H, s), 7.38 (1H, s), 7.08 (1H, s), 6.10 (2H, s).

Part B. 2-Bromo-4,5-methylenedioxybenzaldehyde ethylene acetal

A solution of 2-bromo-4,5-methylenedioxybenzaldehyde (16 g, 70 mmol), ethylene glycol (8.7 g, 14 mmol) and a catalytic amount of toluene sulfonic acid monohydrate (1.0 g) in toluene (450 mL) was heated at boiling point for 1 hour while water was removed with a Dean-Stark apparatus. The mixture was allowed to cool and washed successively with water (200 mL), saturated sodium bicarbonate solution (200 mL), and brine (200 mL). The solution was dried (MgSO$_4$)

and concentrated in vacuo to leave a yellow oil which crystallized from ethyl acetate to give the product (13.7 g, 72%) as a white crystalline solid, mp 69–71° C.

Part C. 3-(Diphenylimino)-N-methoxy-N-methylbenzamide

A solution of 3-nitrobenzoyl chloride (30 g, 0.16 mol) and N,O-dimethylhydroxylamine hydrochloride in dichloromethane (500 mL) was cooled to 0° C. under a nitrogen atmosphere. Pyridine (28 g, 0.36 mol) was added dropwise over 5 min and the resulting suspension was stirred for 16 hours. The volatiles were removed in vacuo and the residue was partitioned between ethyl acetate (300 mL) and water (100 mL). The layers were separated and the organic layer was washed with 1N HCl (2×100 mL), brine (100 mL) and dried ($MgSO_4$). The solvent was removed in vacuo to leave an oil which was used directly.

The crude nitrobenzene was dissolved in methanol (500 mL) and 10% palladium on carbon (1.0 g) was added. The mixture was shaken on a Parr apparatus for 30 min under 45 psi hydrogen atmosphere When hydrogen absorption had ceased (ca. 30 min) the solution was filtered through celite and concentrated in vacuo. The crude amine was used without further purification.

A solution of the amine and benzophenone imine (25 g, 0.14 mol) in toluene (400 mL) at room temperature was treated with a catalytic amount of boron trifluoride etherate (5 mL). The solution was heated to boiling point for 16 hours, cooled to room temperature, and washed successively with saturated sodium bicarbonate solution (300 mL), water (300 mL) and brine (300 mL). The solution was dried ($MgSO_4$) and concentrated in vacuo to give a yellow oil which crystallized from ethyl acetate toc give (16.0 g, 29%) as yellow crystals, mp 104–6° C. $^1$HNMR (200 MHz, $CDCl_3$) δ 7.74 (2H, m), 7.44 (2H, m), 7.30–7.10 (8H, m), 6.96 (1H, m), 6.86 (1H, m), 3.80 (3H, s), 3.40 (3H, s).

Part D. 2-Ethylene acetal-4,5-methylenedioxy-3'-diphenyliminobenzophenone

A solution of 2-bromo-4,5-methylenedioxybenzaldehyde ethylene acetal (3.0 g, 11 mmol) in THF (50 mL) was cooled to −78° C. under a nitrogen atmosphere and a solution of n-butyl lithium in hexanes (1.6 M, 1.1 eq, 7.6 mL, 13.2 mmol) was added. The solution was stirred 10 min and then transferred via cannula to a −78° C. solution of 3-(diphenylimino)-N-methoxy-N-methylbenzamide (1.05 eq, 3.95 g, 11.55 mmol) in THF (50 mL). The resulting mixture was allowed to reach room temperature and stir for 16 hours. Saturated ammonium chloride solution (100 mL) was added and the layers were separated. The aqueous phase was (extracted with ethyl acetate (3×100 mL) and the combined organic phase was washed with brine (200 mL), dried ($MgSO_4$) and concentrated in vacuo to leave an oil which was purified by flash column chromatography on silica oel, eluting with 20% ethyl acetate in hexanes to give (3.0 g, 57%) as a yellow foam, mp 75–77° C. $R_f$ 0.5 (30% ethyl acetate/hexanes). $^1$HNMR (200 MHz, $CDCl_3$) δ 7.75 (2H, m), 7.50–6.90 (15H, m), 6.05 (2H, s), 3.90 (4H, m).

Part E. 1-(3-Aminophenyl)-6,7-methylenedioxyphthalazine

2-Ethylene acetal-4,5-methylenedioxy-3'-diphenyliminobenzophenone was (3.0 g, 6.3 mmol), suspended in methanol (125 mL) and water (12 mL), was treated with hydrazine dihydrochloride (1.1 eq, 0.7:3 g, 6.93 mmol) and hydrazine monohydrate (1.1 eq, 0.34 mL, 6.93 mmol), The resulting suspension was stirred 3 days at room temperature. The volatiles were removed in vacuo and the residue was partitioned between ethyl acetate (100 mL) and water (100 mL). 1N HCl (10 mL) was added and the layers were separated. The aqueous layer was extracted with ethyl acetate (100 mL). The pH of the aqueous layer was adjusted to 10 by the careful addition of 1N NaOH and the aqueous layer was then extracted with dichloromethane (3×100 mL). The combined organic phase was washed witrh brine (200 mL), dried ($MgSO_4$) and concentrated in vacuo to leave an oil which was purified by flash column chromatography on silica gel, eluting with 10% methanol in ethyl acetate to give (651 mg, 39%) as a red amorphous solid, mp 205–208° C. (dec.). $R_f$ 0.5 (20% methanol/ethyl acetate). $^1$H NMR (200 MHz, $CDCl_3$) δ 9.60 (1H, s), 7.40–7.20 (4H, m), 7.05 (2H, m), 6.85 (1H, m), 6.20 (2H, s), 3.80 (2H, brs).

EXAMPLE 49

Synthesis of 1-(4-Aminophenyl)-6,7-methylendioxyphthalazine

Part A. N'-Methoxyl-N'-methyl-4-nitrobenzenecarboxamide

A mixture of p-nitrobenzoyl chloride (30 g, 0.16 mole), N,O,-dimethylhydroxylamine hydrochloride (17 g, 0.18 mole) and methylene chloride (500 mL) were stirred and cooled in an ice bath. Pyridine (28 g, 0.36 mole) was added dropwise over 5 minutes and the mixture stirred an additional 2 hours. The solvents were evaporated in vacuo, the residue was treated with EtOAc (300 mL) and 1N HCl (100 mL) and separated. The aqueous layer was washed with EtOAc (100 mL), the combined organic layers were dried ($MgSO_4$) and evaporated in vacuo to leave a yellow oil that crystallized upon treatment with ether-hexanes. The light yellow solid was collected by filtration, washed (ether-hexanes) and air dried to afford 24 g (71%) of the amide. Mp 71–74 ° C.

Part B. N'-Methoxyl-N'-methyl-4-aminobenzenecarboxamide

N'-Methoxyl-N'-methyl-4-nitrobenzenecarboxamide (22 g, 0.10 mole), 10% palladium on carbon (1.0 g) and methanol (500 ml,) were agitated on a Parr shaker under 45 p.s.i. initial pressure. After 30 minutes no more hydrogen uptake was observed. The catalyst was filtered, washed (methanol) and the filtrate was evaporated in vacuo to afford a tan solid. The solid was chromatographed on silica gel eluting with 33% hexaneq/EtOAc to 25% hexanes/EtOAc. The amine was obtained as a tan solid (19 g, 100%). Mp 91–94° C. 200 MHz $^1$H-NMR ($CDCl_3$); δ 7.63 (d, 2H, J=8.4 Hz, $H^2$), 6.66 (d, 2H, J=8.4 Hz, $H^3$), 3.95 (bs, 2H, $NH_2$), 3.6 (s, 3H, $OCH_3$), 3.34 (s, 3H, $NCH_3$).

Part C. 4-N'-(2',2'-Diphenylimino)-N-methoxyl-N-methylcarboxamide

A mixture of N'-methoxyl-N'-methyl-4-aminobenzenecarboxamide (18 g, 0.10 mole), benzophenone imine (19 g, 0.11 mole), boron trifluoride etherate (5 mL) and toluene (400 mL) was stirred and heated to reflux under a nitrogen atmosphere for 4 hours. The mixture was cooled to ambient temperature and washed with saturated aqueous sodium bicarbonate (100 mL), water (100 mL) and brine (100 mL). The dried ($MgSO_4$) organic layer was evaporated in vacuo to leave a yellow solid that recrystallized from hexanes-EtOAc (23 g, 67%). The filtrate was condensed and chromatographed on silica gel eluting with 25% hexane/EtOAc to 33% hexane/EtOAc to 50% hexane/EtOAc. Another 4.7 g (4%) of product was isolated. Total yield=27.7 g (81%). Mp 123–6° C. 200 MHz $^1$H-NMR ($CDCl_3$); δ 7.53 (d, 2H, J=7.8 Hz, $H^2$), 7.40 (m, 10H, ArH), 6.72 (d, 2H, J=7.8 Hz, $H^3$), 3.50 (s, 3H, $OCH_3$), 3.30 (s, 3H, $NCH_3$).

Part D: 2-(1,3-Dioxolan-2-vl)-4'-diphenylimino-4 5-methylenedioxybenzophenone

An oven dried, 3-necked, 250 mL flask was purged with nitrogen, charged with 5-bromo-6-(1,3-dioxolanyl-2-yl)-2, 3-methylenedioxybenzene (7.5 g, 27 mmole) and THF (80 mL, freshly distilled from sodium benzophenone ketyl). The solution was cooled to −78° C. and n-butyl lithium (12 mL of a 2.5 M solution in hexanes, 30 mmole) was added dropwise over 5 minutes. Two minutes after the addition of butyl lithium was completed the solution was added via cannula to a solution of 4-N'-(2',2'-diphenylimino)-N-methoxyl-N-methylcarboxamide (9.5 g, 27 mmole) and distilled THF (80 mL) in an oven dried, nitrogen purged, 3-necked, 500 mL flask at −78° C. After 15 minutes the dry-ice bath was removed and the mixture stirred 14 hours at 20° C. and then was poured into a mixture of EtOAc (500 mL) and water (200 mL). The layers were separated, the aqueous layer was extracted with EtOAc (100 mL), combined with the earlier organic layer, dried ($MgSO_4$) and evaporated to leave a yellow solid. Recrystallization from EtOAc provided bright yellow needles (8.2 g, 64%). Mp 187–9° C. 200 MHz $^1$H-NMR ($CDCl_3$); δ 7.68 (d, 2H, J=8.4 Hz), 7.40 (m, 10H, ArH), 6.76 (s, 1H), 6.75 (d, 2H, J=8.4 Hz), 6.06 (s, 2H, $OCH_2O$), 5.81 (s, 1H, OCHO), 3.85 (m, 4H, $OCH_2CH2O$): FAB LRMS (mBNA); 478 (M+1).

Part E. 1-(4-Aminophenyl)-6,7-methylendioxyphthalazine 2-(1,3-Dioxolan-2-yl)-4'-diphenylimino-4,5-methylenedioxy-benzophenone (5.7 g, 12 mmole) and hydrazine dihydrochloride (1.4 g, 13 mmole) were dissolved in methanol (250 mL) and water (25 mL). Hydrazine (0.42 g, 13 mmole) was added and the mixture stirred for 16 hours at 20° C. The solvents were evaporated in vacuo to one quarter the original volume, EtOAc (300 mL), water (300 mL) and 1N HCl (10 mL) were added. The organic layer was further washed with water and the combined aqueous layers were neutralized with 1N NaOH. The precipitati was extracted with dichloromethane (4×500 mL), dried ($MgSO_4$) and evaporated to leave a tan solid. The crude product was chromatographed on silica gel eluting with 10% methanol/EtOAc to afford the aminophenylphthalazine as a tan solid (2.2 g, 69%). Mp 221–223° C. (dec.). 200 MHz $^1$H-NMR ($CDCl_3$); δ 9.28 (s, 1H), 7.58 (d, 2H, J=8.6 Hz), 7.41 (s, 1H), 7.21 (s, 1H), 6.84 (d, 2H, J=8.6 Hz), 6.17 (s, 2H, OCHO), 3.90 (bs, 2H, $NH_2$): FAB LRMS (mNBA); 266 (M+1).

EXAMPLE 50

Synthesis of 4-(4-Aminophenyl)-1-methyl-6,7-methylenedioxyphthalazine

Part A: 4-(4-Acetylaminophenyl)-1,2-dihydro-1-methyl-6 7-methylenedioxyphthalazine.

An oven dried, 3-necked, 250 mL flask was purged with nitrogen and charged with 1-(4-acetylaminophenyl)-6,7-methylendioxyphthalazine (1.0 g, 3.3 mmole), distilled THF (30 mL) and TMEDA (10 mL). The suspension was cooled in an ice bath and treated dropwise over five minutes with an ether solution of methyl lithium (9.3 mL of a 1.4 M solution, 13 mmole). The dark brown mixture was stirred for 1 h, treated cautiously with water (5 mL) then dichloromethane (120 mL). The contents of the flask were transferred to a separatory funnel, water (100 mL) was aidded and the layers were separated. The aqueous phase was further extracted with dichloromethane (50 mL), the extracts combined, washed with brine (100 mL), dried ($MgSO_4$) and evaporated in vacuo. The tan foamy residue was dissolved in methanol (20 mL), silica gel was added and the solvent was evaporated to complete dryness. The crude product was chromatographed on silica gel eluted with EtOAc to afford the addition product a light tan crystalline solid (0.53 g, 50%). Mp 236–239° C. 200 MHz $^1$H-NMR ($CDCl_3$); δ 7.59 (s, 4H), 7.26 (brs, 1H, $NHCOCH_3$), 6.75 (s, 1H), 6.73 (s, 1H), 6.00 (s, 2H, OCHO), 5.88 (brs, 1H), 4.31 (q, 1H, J=6.4 Hz, —$CHCH_3$), 2.60 (s, 3H, $COCH_3$), 1.48 (d, 3H, J=6.4 Hz, $CHCH_3$).

Part B: 4-(4-Aminophenyl)-1-methyl-6,7-methylenedioxy-1,2-dihydro-phthalazine 4-(4-Aminophenyl)-6,7-methylenedioxyphthalazine (600 mg, 2.3 mmol) was suspensed in THF (25 mL) at 20° C. in an oven dried 3-necked flask under $N_2$. $CH_3Li$ (6.5 mL, 9.1 mmol) in ether wais added slowly and stirred for 30 min. The reaction was quenched by the addition of 1 N HCl (50 mL) and then extracted with EtOAc (30 mL). The organic layer was extracted again with 1 N HCl (100 mL) and then the combined aqueous layers neutralized with 1 N NaOH. The aqueous mixture was then extracted with $CH_2Cl_2$ (3×50 mL) and the organic layers combined, dried with $K_2CO_3$ and evaporated to give a brown gum. The brown gum vias chromatographed on silica-gel 4:1 EtOAc/hexane to give a yellow gum (320 mg, 50%). 200 MHz $^1$H-NMR ($CDCl_3$); δ 7.64 (d, 2H), 7.35 (d, 2H), 6.56 (d, 2H), 6.06 (s, 2H), 4.29 (q, CH), 1.33 (d, $CH_3$).

Part C. 4-(4-Aminophenyl)-1-methyl-6,7-methylenedioxyphthalazine 4-(4-Aminophenyl)-1-methyl-6,7-methylenedioxyphthalazine (200 mg, 0.71 mmol) and Pd/C (25 mg) were suspended in toluene (15 mL) and heated to reflux under $N_2$ for 10 h. Upon cooling to 20° C. a beige solid appeared and was collected by filtration. Silica gel chromatography (9:1 EtOAc/MeOH) gave a yellow solid, 130 mg, (66%). 200 MHz $^1$H-NMR ($CDCl_3$); δ 7.50 (d, 2H), 7.36 (d, 2H), 6.83 (d, 2H), 6.16 (s, $CH_2$) 2.93 (s, $CH_3$).

EXAMPLE 101

Synthesis of 4-(4-Acetylaminophenyl)-6,7-methylendioxyphthalazine 1-(4-Aminophenyl)-6,7-methylendioxyphthalazine (3.0 g, 11 mmole) and acetic anhydride (50 mL) were stirred at ambient temperature for 3 h. The dark green mixture was cooled in an ice bath and treated with 1N HCl (200 mL). After 30 min the mixture was filtered through celite, neutralized with solid sodium carbonate and the resulting precipitate was filtered, washed with water (3×50 mL) and vacuum dried to leave a tan solid (3.1 g, 92%). A 0.17 g sample was recrystallized from methanol-water to leave a light yellow solid. TLC is homogeneous (20% methanol/EtOAc). Mp 268–270° C. (dec.). 200 MHz $^1$H-NMR (DMSO-$d_6$); δ 10.30 (bra, 1H, NH), 9.53 (s, 1H), 7.93 (d, 2H, J=7.0 Hz), 7.76 (d, 2H, J=7.0 Hz), 7.75 (s, 1H), 7.37 (s, 1H), 6.43 (s, 2H, OCHO), 2.24 (s, 3H, $COCH_3$): CI ($CH_4$) LRMS; 308 (M+1).

Modifications and variations of the present invention will be obvious to those skilled in the art from the foregoing detailed description. Such modifications and variations are intended to come within the scope of the following claims.

What is claimed is:

1. A compound of Formula I

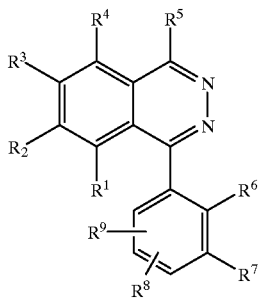

wherein $R^1$, $R^2$, $R^3$ and $R^4$ are independently
a) H,
b) HO,
c) $R^{11}O—$,
d) halogen,
e) C1–C3-alkyl,
f) $CF_3$,
g) $R^{12}CO_2—$, or
h) $R^{12}CONH—$;

$R^1$ and $R^2$, or $R^2$ and $R^3$, or $R^3$ and $R^4$ can be taken together to be
a) $—OCH_2O—$, or
b) $—OCH_2CH_2O—$;

$R^5$ is
a) H,
b) C1–C6-alkyl,
c) C3–C6-alkenyl,
d) C3–C6-alkynyl,
e) C3–C6-cycloalkyl,
f) phenyl or substituted phenyl, wherein the phenyl is substituted with one or two substituents selected from the group consisting of C1–C3-alkyl, halogen, $R^{12}HN—$, $R^{12}O—$, $CF_3—$, $R^{13}SO_2—$ and $CO_2R^{12}$, or
g) phenyl-C1–C3-alkyl or substituted phenyl-C1–C3-alkyl, wherein the phenyl is substituted with one or two substituents selected from the group consisting of C1–C3-alkyl, halogen, $R^{12}HN—$, $R^{12}O—$, $CF_3—$, $R^{13}SO_2—$ and $—CO_2R^{12}$;

$R^6$ is
a) $R^{10}R^{11}N—$,
b) $R^{10}NHC(NH)—$,
c) $R^{12}CONH—$,
d) 1-pyrrolidino or
e) 1-piperidino;

R is H;

$R^8$ and $R^9$ are independently
a) H,
b) C1–C3-alkyl,
c) halogen,
d) $R^{12}O—$,
e) $CF_3—$, or
f) $—CO_2R^{12}$;

$R^{10}$ and $R^{11}$ are independently
a) H,
b) C1–C10-alkyl,
c) C1–C6-perfluoroalkyl,
d) C3–C10-alkenyl,
e) C3–C10-alkynyl, or
f) C3–C6-cycloalkyl;

$R^{12}$ is H or C1–C3-alkyl; and $R^{13}$ is C1–C3-alkyl or $CF_3$;

and pharmaceutically acceptable salts thereof.

2. The compound of claim 1 of Formula I wherein
$R^1$, $R^2$, $R^3$ and $R^4$ are independently H, $R^{11}O—$, halogen, or C1–C3-alkyl;
$R^2$ and $R^3$ taken together can be $—OCH_2O—$;
$R^6$ is $R^{10}R^{11}N$;
$R^8$ and $R^9$ are H; and
pharmaceutically acceptable salts thereof.

3. A compound selected from the group consisting of
1-(2-aminophenyl)-6,7-methylenedioxyphthalazine,
1-(2-amino-4-methylphenyl)-6,7-methylenedioxyphthalazine,
1-(2-amino-4-chlorophenyl)-6,7-methylenedioxyphthalazine,
1-(2-aminophenyl)-6-methoxyphthalazine,
1-(2-amino-4-methylphenyl)-6-methoxyphthalazine,
1-(2-amino-4-chlorophenyl)-6-methoxy-phthalazine,
1-methyl-4-(2-aminophenyl)-6,7-methylenedioxyphthalazine,
1-methyl-4-(2-amino-4-methylphenyl)-6,7-methylenedioxyphthalazine,
1-methyl-4-(2-amino-4-chlorophenyl)-6,7-methylenedioxyphthalazine,
1-ethyl-4-(2-aminophenyt)-6,7-methylenedioxyphthalazine,
1-methyl-4-(2-aminophenyl)-6-methoxyphthalazine,
1-methyl-4-(2-amino-4-methylphenyl)-6-methoxyphthalazine,
1-methyl-4-(2-amino-4-chlorophenyl)-6-methoxyphthalazine, and
1-ethyl-4-(2-aminophenyl)-6-methoxyphthalazine.

4. A pharmaceutical composition comprising the compound of claim 2 in combination with a pharmaceutically acceptable carrier.

5. A pharmaceutical composition comprising the compound of claim 3 in combination with a pharmaceutically acceptable carrier.

6. A pharmaceutical composition comprising a compound of Formula II:

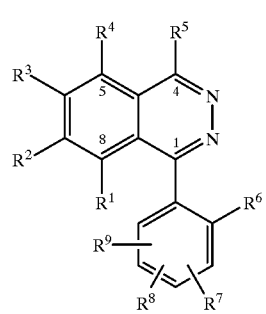

wherein $R^1$, $R^2$, $R^3$ and $R^4$ are independently
a) H,
b) HO,
c) $R^{11}O—$,
d) halogen, e) C1–C3-alkyl,
f) $CF_3$,
g) $R^{12}CO_2$—, or
h) $R^{12}CONH$—;

$R^1$ and $R^2$, or $R^2$ and $R^3$, or $R^3$ and $R^4$ can be taken together to be
a) —$OCH_2O$—, or
b) —$OCH_2CH_2O$—;

$R^5$ is
a) H,
b) C1–C6-alkyl,
c) C3–C6-alkenyl,
d) C3–C6-alkynyl,
e) C3–C6-cycloalkyl,
f) phenyl or substituted phenyl, where the phenyl is substituted with one or two substituents, C1–C3-alkyl, halogen, $R^{12}HN$—, $R^{12}O$—, $CF_3$—, $R^{13}SO_2$— or $CO_2R^{12}$, or
g) phenyl-C1–C3-alkyl or substituted phenyl-C1–C3-alkyl, where the phenyl is substituted with one or two substituents, C1–C3-alkyl, halogen, $R^{12}HN$—, $R^{12}O$—, $CF_3$—, $R^{13}SO_2$— or, —$CO_2R^{12}$, $R^6$ and $R^7$ are independently
a) H
b) $R^{10}R^{11}N$—,
c) $R^{10}NHC(NH)$—,
d) $R^{12}CONH$—
e) 1-pyrrolidino or
f) 1-piperidino;

$R^8$ and $R^9$ are independently
a) H,
b) C1–C3-alkyl,
c) halogen,
d) $R^{12}O$—,
e) $CF_3$—, or
f) —$CO_2R^{12}$;

$R^{10}$ and $R^{11}$ are independently
a) H,
b) C1–C10-alkyl,
c) C1–C6-perfluoroalkyl,
d) C3–C10-alkenyl,
e) C3–C10-alkynyl, or
f) C3–C6-cycloalkyl;

$R^{12}$ is H or C1–C3-alkyl; and $R^{13}$ is C1–C3-alkyl or $CF_3$;

and pharmaceutically acceptable salts thereof with the proviso that $R^6$ and $R^7$ cannot both be H, in combination with a pharmaceutically acceptable carrier.

7. A composition comprising a compound selected from the group consisting of 1-(3-aminophenyl)-6,7-methylenedioxyphthalazine,
1-(3-amino-4-methylphenyl)-6,7-methylenedioxyphthalazine,
1-(3-amino-4-chlorophenyl)-6,7-methylenedioxyphthalazine,
1-(3-aminophenyl)-6-methoxyphthalazine,
1-(3-amino-4-methylphenyl)-6-methoxyphthalazine,
1-(3-amino-4-chlorophenyl)-6-methoxy-phthalazine,
1-methyl-4-(3-aminophenyl)-6,7-methylenedioxyphthalazine,
1-methyl-4-(3-amino-4-methylphenyl)-6,7-methylenedioxyphtlalazine,
1-methyl-4-(3-amino-4-chlorophenyl)-6,7-methylenedioxyphttalazine,
1-ethyl-4-(3-aminophenyl)-6,7-methylenedioxyphthalazine,
1-methyl-4-(3-aminophenyl)-6-methoxyphthalazine,
1-methyl-4-(3-amino-4-methylphenyl)-6-methoxyphthalazine,
1-methyl-4-(3-amino-4-chlorophenyl)-6-methoxyphthalazinc, and
1-ethyl-4-(3-aminophenyl)-6-methoxyphthalazine, in combination with a pharmaceutically acceptable carrier.

8. The composition of claim 6 comprising an effective amount of the compound of Formula II for treating a disorder in a patient associated with excessive activation of the α-amino-3-hydroxy-5-methyl-4-isooxazoleproprionic acid (AMPA) subtype of the ionotropic excitatory amino acid (EAA) receptors.

9. A composition comprising a pharmaceutically acceptable carrier and an effective amount of the compound of claim 2 for treating a disorder in a patient associated with excessive activation of the α-amino-3-hydroxy-5-methyl-4-isooxazoleproprionic acid (AMPA) subtype of the ionotropic excitatory amino acid (EAA) receptors.

10. A composition comprising a pharmaceutically acceptable carrier and an effective amount of the compound of claim 3 for treating a disorder in a patient associated with excessive activation of the α-amino-3-hydroxy-5-methyl-4-isooxazoleproprionic acid (AMPA) subtype of the ionotropic excitatory amino acid (EAA) receptors.

11. The composition of claim 7 comprising an effective amount of the compound of Formula II for treating a disorder in a patient associated with excessive activation of the α-amino-3-hydroxy-5-methyl-4-isooxazoleproprionic acid (AMPA) subtype of the ionotropic excitatory amino acid (EAA) receptors.

* * * * *